United States Patent [19]

Heimbach et al.

[11] 4,163,024

[45] Jul. 31, 1979

[54] PROCESS FOR CONTROLLING THE CATALYTIC CO-OLIGOMERIZATION OF 1,3-DIENES WITH SCHIFF'S BASES

[75] Inventors: Paul Heimbach; Achim Roloff; Erich F. Nabbefeld-Arnold, all of Mülheim, Fed. Rep. of Germany

[73] Assignee: Studiengesellschaft Kohle mbH., Mülheim, Fed. Rep. of Germany

[21] Appl. No.: 820,962

[22] Filed: Aug. 1, 1977

[30] Foreign Application Priority Data

Aug. 26, 1976 [DE] Fed. Rep. of Germany ....... 2638430

[51] Int. Cl.$^2$ .......................................... C07C 119/00
[52] U.S. Cl. ........................... 260/566 R; 260/566 F; 260/568; 260/570.5 R; 260/570.5 P; 260/570.5 CA; 260/571; 260/583 H; 260/563 R; 260/563 P
[58] Field of Search ............... 260/566 R, 566 F, 568, 260/570.5 R, 570.5 P, 570.5 CA, 571, 583 H, 563 R, 563 P

[56] References Cited

U.S. PATENT DOCUMENTS 2,686,209 8/1954 Reed ................................. 260/666 B

FOREIGN PATENT DOCUMENTS 881511 6/1953 Fed. Rep. of Germany .
1144268 2/1963 Fed. Rep. of Germany .
1140569 10/1966 Fed. Rep. of Germany .
1126864 6/1967 Fed. Rep. of Germany .
1493221 4/1973 Fed. Rep. of Germany .
2507007 9/1975 Fed. Rep. of Germany .

*Primary Examiner*—Gerald A. Schwartz
*Attorney, Agent, or Firm*—Sprung, Felfe, Horn, Lynch & Kramer

[57] ABSTRACT

A process has been developed for controlling the catalytic co-oligmoerization of 1,3-dienes with Schiff's bases which comprises condensing a 1,3-diene of the formula

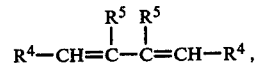

wherein $R^4$ and $R^5$, independently of one another, represent hydrogen or an alkyl group having 1 to 4 carbon atoms with a Schiff base of the formula

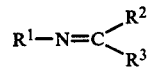

wherein each of $R^1$, $R^2$ and $R^3$ represents hydrogen alkyl, cycloalkyl, aralkyl, aryl or dimethylamino groups which, in addition, optionally contain functional groups of the group consisting of ethers esters, C=N double bonds and which can be closed to form a ring, in the presence of a nickel (O)-containing catalyst, and optionally in the presence of an X—H compound with a molar ratio of Ni: X H of from 1:0 to 1:10.

4 Claims, No Drawings

PROCESS FOR CONTROLLING THE CATALYTIC CO-OLIGOMERIZATION OF 1,3-DIENES WITH SCHIFF'S BASES

This invention relates to a process for controlling the catalytic co-oligomerisation of two molecules of 1,3-diene with Schiff's bases I

                                                                    I to form "octatrienylated" amines II or "octadienylated" Schiff's bases III:

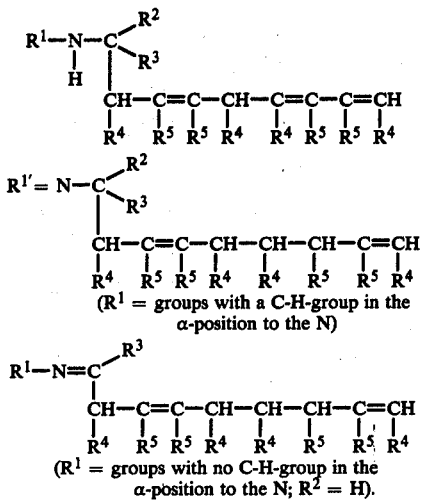

In the above formulae, $R^1$, $R^2$ and $R^3$ may represent hydrogen and/or alkyl, cycloalkyl, aralkyl or aryl radicals or dimethylamino groups which, in addition, can contain functional groups, such as ethers, esters, C=N-double bonds etc., and can be closed to form a ring, and $R^4$ and $R^5$ independently of one another represent hydrogen or an alkyl group with 1 to 4 carbon atoms.

German Patent Specification No. 1,140,569 describes a process for the catalytic dimerisation or trimerisation of 1,3-diolefins using catalysts produced by mixing compounds of nickel free from carbon monoxide with organometallic compounds, such as metal alkyls, metal aryls, Grignard compounds, or with metal hydrides or with metal hydride complex compounds and electron donors. The electron donors used are Lewis bases, such as cyclic ethers, tertiary amines, especially cyclic tertiary amines, alkyl or aryl phosphines, especially triphenyl phosphine, or alkyl or aryl phosphites or compounds containing a carbon-carbon multiple bond. Similar processes are claimed in German Auslegeschrift Nos. 1,126,864 (where the catalysts are produced by reducing transition metal compounds with metals such as Al, Mg) and 1,144,268 (where certain nickel-(O)-compounds are used as catalysts). In addition, it is known that butadiene can be converted into mixtures of 1,5-cyclooctadiene and 4-vinyl cyclohexene(+) in the presence of catalysts, such as $(R_3P)_2Ni(CO)_2$, by the processes described in German Patent Specification No. 881,511 and U.S. Patent Specification No. 2,686,209.
(+) In the following disclosure, COD=1,5-cyclooctadiene, VCH=4-vinylcyclohexene, CDT=1,5,9-cyclododecatriene In addition, it is known from Belgian Patent Specification No. 622,195 and German Patent Specification No. 1,493,221 that 1,3-diolefins can be co-oligomerized with unsaturated compounds to form 2:1-adducts.

German Offenlegungsschrift No. 25 07 007 describes the production of compounds corresponding to general formulae II and IIIa.

It has now surprisingly been found that 1,3-dienes corresponding to the general formula

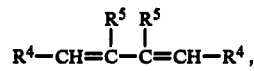
                                                                    IV in which $R^4$ and $R^5$ independently of one another represent hydrogen or an alkyl group containing from 1 to 4 carbon atoms, can be reacted with Schiff's bases of general formula I, in which $R^1$, $R^2$ and $R^3$ represent hydrogen and/or alkyl, cycloalkyl, aralkyl or aryl radicals, or dimethylamino groups, and which in addition contain functional groups, such as ethers, esters, C=N-double bonds etc. and can be closed to form a ring, in the presence of catalysts to form open-chain 2:1-adducts either of the type II or of the type IIIa or IIIb by controlling the catalytic co-oligomerization reaction in the presence of compounds of non-valent nickel with or without electron donors by the exclusion of or by the addition of X-H-compounds. Whereas compounds of type IIIa or IIIb are formed in the absence of this addition, the effect of adding the H-acid compounds is that compounds of type II are formed. If the concentration of H-acid compounds added falls below a certain limit, both types can be formed alongside one another.

As defined above, $R^1$, $R^2$ and $R^3$ preferably represent hydrogen and/or alkyl having 1 to 12 carbon atoms (more specifically 1 to 7 carbon atoms), such as methyl, ethyl, propyl, butyl, isobutyl, tertiary-butyl, amyl, hexyl, octyl and dodecyl; cycloalkyl having 5 to 7 ring members, such as cyclopentyl, cyclohexyl and cycloheptyl; aralkyl in which the aryl portion is carbocyclic and has up to 10 ring members and the alkyl portion has up to 7 carbon atoms, such as benzyl, phenethyl, phenyl-propyl, naphthylmethyl and naphthyl-ethyl, and aryl is carbocyclic and has up to 10 ring members, such as phenyl, tolyl, xylyl, naphthyl; or the dimethylamino group, and which, in addition, optionally contain functional groups, such as ethers, for example alkyl ethers having up to 12, preferably up to 7 carbon atoms, esters, such as alkyl esters having up to 12, preferably up to 7 carbon atoms, C=N double bonds, etc., and can be closed to form an alkyleneimino ring having 5 to 7 ring members.

The following open-chain 2:1 adducts for example may be produced by the process according to the invention:

Either:

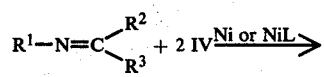

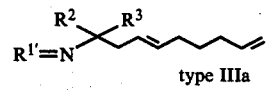
                                                            type IIIa $R^1$=groups containing hydrogen in the α-position to the N,

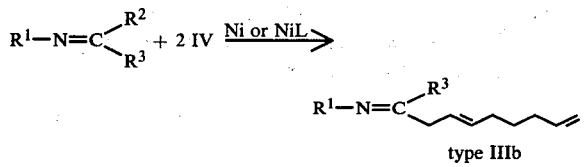

$R^1$ = groups with no hydrogen in the α-position to the N; $R^2$ = H.

These products are obtained when the reaction mixture is free from X—H-compounds by carefully purifying the substrates and solvents. Reaction products of type IIIa are always preferentially formed when hydrogen atoms are attached to the carbon atom in the α-position to the N of the original C=N-double bond, whereas reaction products of type IIIb are formed when there are no hydrogen atoms in the α-position to the N of the original C=N-double bond and $R^2$ and $R^3$ = H.

Or:

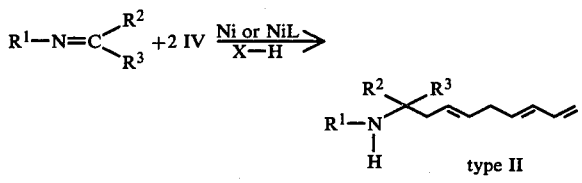

In this case, conjugated trienes of the type V

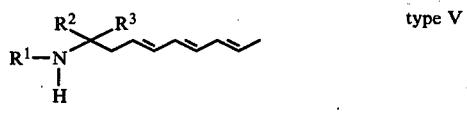

are formed, particularly in the case of sterically demanding substituents $R^1$, such as for example isopropyl groups, dimethylamino groups, and with high conversions of the 1,3-diene.

According to the invention, products of type II or III are obtained by adding X—H—compounds to the reaction mixture in a molar ratio of Ni:X—H of 1:10⁻³ to 1:10². The X—H—compounds used may be, in particular, weakly H-acid compounds, such as primary and secondary amines and phosphanes, alcohols, organic acids, water etc.

Thus, the weakly H-acid compounds are preferably primary and secondary amines, such as alkylamines or dialkylamines having up to 12 (preferably up to 7) carbon atoms, cycloalkyl amines having 4 to 8 ring members, such as cyclobutylamine, cyclopentylamine, cyclohexylamine, cycloheptylamine; carbocyclic arylamines having up to 10 ring members, such amino-substituted benzenes or naphthalenes, such as aniline, N-alkyl-anilines having up to 7 carbon atoms in the alkyl portion of N-alkylnaphthalenes having up to 7 carbon atoms in the alkyl portion; mono- or di-aza-cyclic carbocyclic amines having 5 to 7 ring members, such as piperidine, piperazine, etc; monooxa- monoazacarbocyclic amines; unsaturated carbocyclic cycloaliphatic amines having up to 3 double bonds and iptionally N-alkylated wherein the N-alkyl portion has up to 7 carbon atoms, such as, cyclopentenylamine, cyclohexenylamine, N-methyl-cyclohexenylamine, N-propylamino 1,3,6-octatriene, etc; phosphanes, such as alkyl or dialkyl phosphanes in which each alkyl group contains up to 12, preferably up to 7 carbon atoms, aryl, such as phenyl- or naphthyl-substituted phosphanes, alkyl-aryl phosphanes, particularly wherein alkyl has up to 7 carbon atoms and aryl is phenyl or naphthyl; alcohols, such as alkanols having up to 5 carbon atoms, cycloalkanols, having 5 to 7 ring members, such as cyclopentanol, cyclohexanol and cycloheptanol; organic acids, such as alkane mono-carboxylic and alkane di-carboxylic acids, in which the alkyl portion has up to 7 carbon atoms.

It is possible to use, for example, amines such as morpholine, N-methyl aniline, piperidine, piperazine, pyrrolidine, diethylamine, cyclohexylamine, propylamine, aniline, 9-propylamino-1,3,6-octatriene, etc.; alcohols such as methanol, ethanol, tert.-butanol, cyclohexanol, phenol, etc.; phosphanes such as isopropyl phenyl phosphane, diphenyl phosphane, phenyl phosphane, diisopropyl phosphane, cyclohexyl phosphane, etc.; organic acids such as acetic acid, propionic acid, adipic acid, etc. In cases where secondary phosphanes are used, it is advisable to use nickel-ligand catalysts.

The dependence of the composition of the products upon the molar ratio of Ni to X—H is shown in FIG. 1 for the case where X—H=morpholine. The experimental data for the points 6, 4 and 1 are shown in Examples 1, 2 and 3.

| Ex. | Molar Ratio of Morpholine to Ni | Σ Amine II | +Schiff's Base III = 100% Amine II | Schiff's Base of Type III |
|---|---|---|---|---|
| 3 | ① 11.5 : 8.7 = 1.32 | | 100% | 0% |
|   | ② 1.15 : 9.1 = 1.1 · 10⁻¹ | | 91.1% | 8.9% |
|   | ③ 1.15 · 10⁻¹ : 9.1 = 1.1 · 10⁻² | | 92.7% | 7.3% |
| 2 | ④ 8.0 · 10⁻² : 9.5 = 8.5 · 10⁻³ | | 88.4% | 11.6% |
|   | ⑤ 8.0 · 10⁻³ : 10.5 = 7.6 · 10⁻⁴ | | 15.1% | 84.9% |
| 1 | ⑥ 0 + 10.5 = 0 | | 0% | 100% |

FIG. 1: Dependence of product composition in the co-oligomerisation of N-benzylidene propylamine and butadiene on a nickel-triphenyl phosphane catalyst upon the molar ratio of Ni to morpholine at a reaction temperature of 40° C.

The 1,3-diolefins used in the process according to the invention are, primarily, isoprene, piperylene and, in particular, 1,3-butadiene, although it is also possible to use other 1,3-diolefins, such as 3-methyl-1,4,6-heptatriene, 2,3-dimethyl-1,3-butadiene, 1,3-pentadiene and 1,3,6-octatriene. It is also possible to react various 1,3-diolefins with one another.

The following Schiff's bases for example can be used in the process according to the invention:
(1) N-ethylidene butylamine
(2) N-butylidene propylamine
(3) N-isopropylidene butylamine
(4) N-isopropylidene isopropylamine
(5) N-cyclohexylidene propylamine
(6) N-benzylidene methylamine
(7) N-benzylidene ethylamine
(8) N-benzylidene-n-propylamine
(9) N-benzylidene isopropylamine
(10) N-benzylidene butylamine

(11) N-benzylidene-sec.-butylamine
(12) N-benzylidene isopropylamine
(13) N-(1-butylpentylidene)-n-propylamine
(14) N-benzylidene neopentylamine
(15) N-benzylidene cyclohexylamine
(16) N-(4-methoxybenzylidene)-isopropylamine
(17) acetaldehyde dimethyl hydrazone
(18) glyoxal-bis-dimethyl hydrazone.

The compounds of nickel mentioned in the Patent Specifications referred to above are used as catalysts.

An excess of reducing agents such as, for example, aluminium triethyl, diethyl aluminium hydride, lithium aluminium hydride or even the presence of Lewis acids, such as BF$_3$-etherate for example, leads in fluctuating yields to the formation of "octadienylated amines" (dihydro compounds):

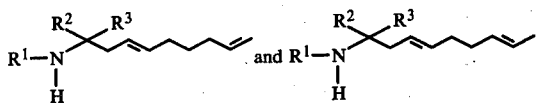

The process according to the invention may be carried out in the presence of solvents, but only those of the kind which do not attack the catalysts. It is preferred to use aliphatic or aromatic hydrocarbons, aliphatic or cycloaliphatic ethers. However, it is of particular advantage to use the diolefins originally used for producing the catalysts or the products obtainable by the process as solvents so that no foreign substances have to be removed from the reaction product. The process may be carried out under normal pressure or even at elevated pressure. The pressure range from 0 to 30 atmospheres is determined by the required course of the reaction and by the particular temperature required. The process may be carried out at temperatures in the range from −10° to +200° C. although it is preferably carried out at temperatures in the range from 20° to 120° C.

It is advisable for the conversion of butadiene not appreciably to exceed 80% because otherwise the 2:1-adducts formed undergo further reaction. In addition, in the event of complete reaction of the butadiene, the "octatrienylated amines" undergo subsequent isomerisation, depending upon the nature of the radicals $R^1$, $R^2$ and $R^3$.

The products obtainable by the process according to the invention are valuable starting materials for further organic syntheses:

1. The "octadienylated amines" can be reacted on nickel-ligand catalysts to form α,ω-bifunctional derivatives.

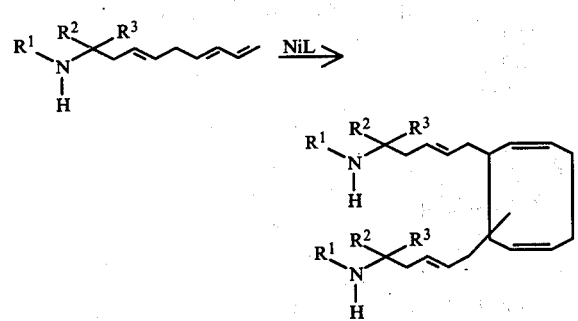

2. The Schiff's bases of type IIIa and IIIb can be hydrolytically decomposed so that, starting from the production of the Schiff's base originally used, the following types of compounds can be obtained by way of the catalytic co-oligomerisation step, followed by hydrolysis:

(a) oxo compounds (aldehydes and ketones) can be aminated by way of the compounds of type IIIa with introduction of an octadienyl group:

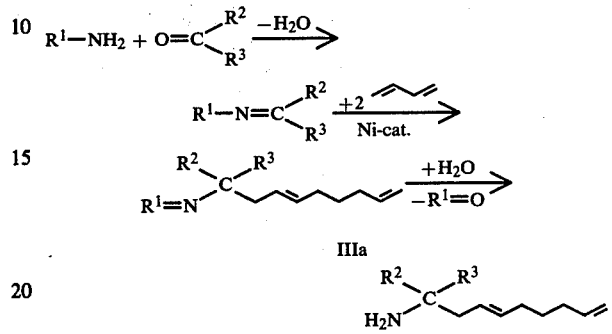

(b) ketones in which the aldehyde hydrogen has been replaced by an octadienyl group are formed from aldehydes by way of the compound IIIb:

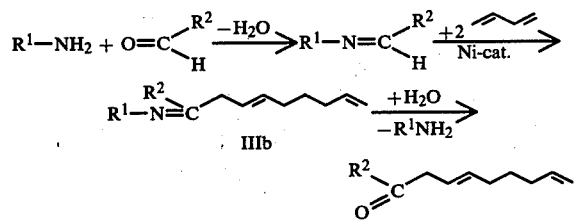

3. As described in DOS No. 2,507,007, all the 2:1-adducts II–IV give the corresponding amine by complete hydrogenation:

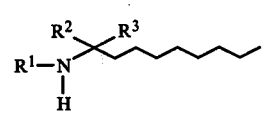

4. In addition, the products obtainable by the process according to the invention can be used for controlling harmful microorganisms by virtue of their antimicrobial activity. For example, they are suitable for protecting materials and organic substrates against attack by harmful and pathogenic microorganisms. They are suitable for use as preservatives and disinfectants for commercial products of all kind.

They are also suitable for use in preserving and disinfecting finishes for plastics, for example polyamides and polyvinyl chloride, and for fibres and textile materials of natural or synthetic origin.

The products obtained by the process according to the invention may be used either individually or in combination with other agents for all those applications which are described from pages 65 to 78 of DT-OS No. 2,507,007.

EXAMPLE 1

In a 250 ml ampoule, 2.9 g (10.5 mMole) of bis-b 1,5-cyclooctadiene nickel and 2.75 g (10.5 mMole) of triphenyl phosphane are dissolved in 93.8 g of toluene under argon as inert gas, followed by the addition at −10° C. of a mixture of 28.7 g of butadiene and 36.7 g of N-benzylidene propylamine. The mixture was heated to +40° C. and stirred at that temperature for a period of 22 hours during which a maximum pressure of 1.5 atmospheres ocurred. All the volatile constituents were then distilled off in vacuo. Bath temperatures of 100° C. were not appreciably exceeded towards the end of distillation at $10^{-4}$ Torr. The composition of the distillate was determined by gas chromatography.

The 2:1 co-oligomer of 2 molecules butadiene and 1 molecule of Schiff's base can be separated off by distillation (b.p. 75° C./$10^{-4}$ Torr; $n_D^{20}$=1.5230).

Conversion of butadiene: 99%
Conversion of N-benzylidene-n-propylamine: 59%
Yield of 9-propylidene amino-9-phenyl-1,6-nonadiene, based on the N-benzylidene propylamine reacted: 62%

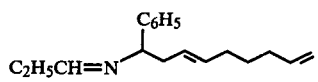

according to $^1$H—NMR—, MS— and IR-spectra, the compound is N-propylidene-9-phenyl-1,6-nonadienylamine.

$^1$H-NMR-spectrum (60 MHz) τ [ppm]: 2.4 (t); 2.8 (m); 4.3 (m); 4.7 (m); 5.1 (m); 4.0 (t); 7.6 (m); 8.0 (m); 8.6 (m); 9.0 (t)
Ratio 1:5:1:2:2:4:4:1:2:4
IR-spectrum (film): 1637, 1600, 1588 cm$^{-1}$ (C=C), 965 cm$^{-1}$ (C=C trans), 906, 990 cm$^{-1}$ (HC=CH$_2$), 1665 cm$^{-1}$ (>C=N—)
Ms (70 eV): m/e=255 (M+); 240 (M—CH$_3$); 146 (M-109).
$C_{18}H_{25}N$
Observed C: 84.8 H: 9.86 N: 5.56
Calculated C: 84.65 H: 9.87 N: 5.48.

EXAMPLE 2

As Example 1, except
Mixture:

2.6 g (9.5 mMole) of bis-1,5-cyclooctadiene nickel
2.65 g (10.1 mMole) of triphenyl phosphane
18.95 g (351 mMole) of butadiene
24.65 g (168 mMole) of N-benzylidene-n-propylamine
0.007 g (0.8 mMole) of morpholine
39.6 g of toluene.
Reaction Temperature: 40° C.
Reaction time: 5 h
Conversion of butadiene: 99.7%
Conversion of N-benzylidene-n-propylamine: 80%
Yield of 9-propylamino-9-phenyl-1,3,6-nonatriene, based on the N-benzylidene-n-propylamine reacted: 25%

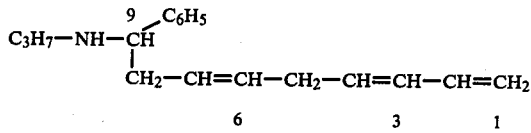

EXAMPLE 3

As Example 1, except
Mixture:
2.4 g (8.7 mMole) of bis-1,5-cyclooctadiene nickel
2.45 g (9.3 mMole) of triphenyl phosphane
26.45 g (499 mMole) of butadiene
23.9 g (163 mMole) of N-benzylidene propylamine
1.0 g (11.5 mMole) of morpholine
24.6 g of toluene.
Reaction temperature: 40° C.
Reaction time: 2 h
Conversion of butadiene: 100%
Conversion of N-benzylidene-n-propylamine: 100%
Yield of 9-propylamino-9-phenyl-1,3,6-nonatriene, based on the N-benzylidene-n-propylamine: 46%.

EXAMPLE 4

As Example 1, except
Mixture:
1.3 g (4.7 mMole) of bis-1,5-cyclooctadiene nickel
1.25 g (4.8 mMole) of tri-phenyl phosphane
24.5 g (454 mMole) of butadiene
28.25 g (192 mMole) of N-benzylidene-n-propylamine
0.06 g (0.9 mMole) of acetic acid
28.3 g of toluene.
Reaction temperature: 40° C.
Reaction time: 170 mins.
Conversion of butadiene: 58%
Conversion of N-benzylidene-n-propylamine: 40%
Yield of 9-propylamino-9-phenyl-1,3,6-nonatriene, based on the N-benzylidene-n-propylamine: 22%
Yield of 9-propylidene amino-9-phenyl-2,6-nonadiene, based on the N-benzylidene-n-propylamine: 49%

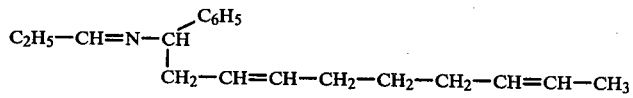

EXAMPLE 5

As Example 1, except
Mixture:
2.5 g (9.1 mMole) of bis-1,5-cyclooctadiene nickel
2.4 g (9.3 mMole) of triphenyl phosphane
49.1 g (909 mMole) of butadiene
74.7 g (562 mMole) of N-benzylidene-n-propylamine
0.25 g (4.2 mMole) of acetic acid
78 g of toluene.
Reaction temperature: 40° C.
Reaction time: 29 h
Conversion of butadiene: 60%
Conversion of N-benzylidene-n-propylamine: 68%
Yield of 9-propylamino-9-phenyl-1,3,6-nonatriene, based on the N-benzylidene-n-propylamine: 65%.

EXAMPLE 6

As Example 1, except

Mixture:
- 2.85 g (10.4 mMole) of bis-1,5-cyclooctadiene nickel
- 2.75 g (10.5 mMole) of triphenyl phosphane
- 39.0 g (722 mMole) of butadiene
- 69.25 g (249 mMole) of N-benzylidene-n-propylamine
- 1.6 g (10.5 mMole) of phenyl isopropyl phosphane
- 69.25 g of toluene.

Reaction temperature: 40° C.
Reaction time: 220 mins.
Conversion of butadiene: 62%
Conversion of N-benzylidene-n-propylamine: 79%
Yield of 9-propylamino-9-phenyl-1,3,6-nonatriene, based on the N-benzylidene propylamine: 66%.

EXAMPLE 7

As Example 1, except
Mixture:
- 1.1 g (4.0 mMole) of bis-1,5-cyclooctadiene nickel
- 1.05 g (4.0 mMole) of triphenyl phosphane
- 18.8 g (348 mMole) of butadiene
- 26.2 g (178 mMole) of N-benzylidene-n-propylamine
- 0.13 g (4 mMole) of methanol
- 29.6 g of toluene.

Reaction temperature: 40° C.
Reaction time: 2 h
Conversion of butadiene: 100%
Conversion of N-benzylidene propylamine: 95%
Yield of 9-propylamino-9-phenyl-1,3,6-nonatriene, based on the N-benzylidene propylamine: 50%.

EXAMPLE 8

As Example 1, except
Mixture:
- 3.85 g (14.0 mMole) of bis-1,5-cyclooctadiene nickel
- 5.65 g (21.6 mMole) of triphenyl phosphane
- 29.2 g (541 mMole) of butadiene
- 32.05 g (218 mMole) of N-benzylidene-n-propylamine
- 0.2 g (11.1 mMole) of water
- 80.35 g of toluene Reaction temperature: 40° C.
Reaction time: 3 h
Conversion of butadiene: 99%
Conversion of N-benzylidene propylamine: 80%
Yield of 9-propylamino-9-phenyl-1,3,6-nonatriene, based on the N-benzylidene propylamine: 56%.

EXAMPLE 9

As Example 1, except
Mixture:
- 2.4 g (8.7 mMole) of bis-1,5-cyclooctadiene nickel
- 2.3 g (8.8 mMole) of triphenyl phosphane
- 28.5 g (528 mMole) of butadiene
- 33.3 g (227 mMole) of N-benzylidene-n-propylamine
- 3.2 g (14.5 mMole) of 9-propylamino-1,3,6-dodecatriene
- 90.0 g of toluene.

Reaction temperature: 40° C.
Reaction time: 95 mins.
Conversion of butadiene: 39%
Conversion of N-benzylidene-n-propylamine: 37%
Yield of 9-propylidene amino-9-phenyl-2,6-nonadiene, based on the N-benzylidene-n-propylamine: 50%

Yield of 9-propylamino-9-phenyl-1,3,6-nonatriene, based on the N-benzylidene-n-propylamine: 29%

At temperatures of 80° C., 9-propylidene amino-9-phenyl-2,6-nonadiene is formed in a yield of 76% with less than 3% of 9-propylamino-9-phenyl-1,3,6-nonatriene, based on the N-benzylidene-n-propylamine reacted.

EXAMPLE 10

As Example 1, except
Mixture:
- 2.5 g (9.8 mMole) of bis-1,5-cyclooctadiene nickel
- 2.65 g (10.1 mMole) of triphenyl phosphane
- 36.3 g (670 mMole) of butadiene
- 55.1 g (340 mMole) of N-benzylidene butylamine
- 65.6 g of toluene.

In all, 5.9 g of VCH, 10.4 g of COD and 21.2 g of 9-(N-butylidene amino)-9-phenyl-1,6-nonadiene are obtained after a reaction time of 22 hours at 60° C.
Conversion of butadiene: 98%
Conversion of N-benzylidene butylamine: 60%
Yield of 9-(N-butylamino)-9-phenyl-1,6-nonadiene, based on the N-benzylidene butylamine reacted: 60%.

The co-oligomer can be separated off by distillation (b.p. 81° C./$10^{-3}$ Torr). According to $^1$H—NMR—, IR— and MS-spectra, the compound is 9-(N-butylidene amino)-9-phenyl-1,6-nonadiene.

$^1$H-NMR-spectrum (60 MHz) $\tau$ [ppm]: 2.4 (t); 2.8 (m); 4.2 (m); 4.6 (m); 5.1 (m), 5.9 (m); 7.5 (m); 8.0 (m); 8.6 (m); 9.1 (t)
Ratio: 1:5:1:2:2:1:2:6:4:3
IR-spectrum (film): 1665 cm$^{-1}$ (>C=N—); 1638 cm$^{-1}$ (C=C); 908; 990 cm$^{-1}$ (HC=CH$_2$); 996 cm$^{-1}$

MS (70 eV): m/e=269 (M$^+$); 226 (M-C$_4$H$_7$); 160 (M-C$_8$H$_{13}$)

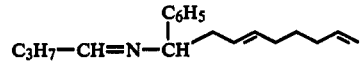

EXAMPLE 11

As Example 1, except
Mixture:
- 2.75 g (10.0 mMole) of bis-1,5-cyclooctadiene nickel
- 39.7 g (735 mMole) of butadiene
- 60.2 g (374 mMole) of N-benzylidene-n-butylamine
- 0.85 mg (~0.01 L mMole) of morpholine
- 84.85 g of toluene.

Reaction temperature: 40° C.
Reaction time: 29 h
Conversion of butadiene: 98%
Conversion of N-benzylidene-n-butylamine: 92%
Yield of 9-butylamino-9-phenyl-1,3,6-nonatriene, based on the N-benzylidene butylamine: 30%
Yield of 9-butylidene amino-9-phenyl-2,6-nonadiene, based on the N-benzylidene butylamine: 24%.

EXAMPLE 12

As Example 1, except
Mixture:
- 2.6 g (9.5 mMole) of bis-1,5-cyclooctadiene nickel 2.5 g (9.5 mMole) of triphenyl phosphane
36.25 g (671 mMole) of butadiene
55.8 g (347 mMole) of N-benzylidene butylamine
8.25 g (95 mMole) of morpholine
87.8 g of toluene.
Reaction temperature: 110° C.
Reaction time: 150 mins.
Conversion of butadiene: 100%
Conversion of N-benzylidene butylamine: 91%
Yield of 9-butylamino-9-phenyl-1,3,6-nonatriene, based on the N-benzylidene butylamine: 65%.

EXAMPLE 13

As Example 1, except
Mixture:
2.8 g (10.19 mMole) of bis-1,5-cyclooctadiene nickel
2.7 g (10.3 mMole) of triphenyl phosphane
38.6 g (715 mMole) of butadiene
48.6 g (349.8 mMole) of cyclohexylidene propylamine
85.8 g of toluene.
Reaction temperature: 100° C.
Reaction time: 1.3 h
Conversion of butadiene: 98%
Conversion of N-cyclohexylidene propylamine: 95%
Yield of 1-propylidene amino-1-(2,7-octadienyl)-cyclohexane, based on the cyclohexylidenepropylamine: 68% $C_{17}H_{30}N$
IR-spectrum: 1636 cm$^{-1}$ (HC=CH$_2$); 968 cm$^{-1}$

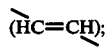
(HC=CH);

1662 cm$^{-1}$ (>C=N—)
$^1$H-NMR-spectrum (60 MHz) τ [ppm]: 2.5 (t); 4.1 (m); 4.65 (m); 5.0 (m); 7.7 (m); 7.9 (m); 8.6 (m); 8.9 (t)
Ratio: 1:1:2:2:2:8:10:3

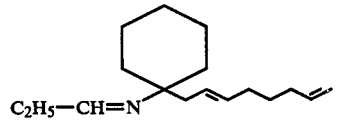

EXAMPLE 14

As Example 1, except
Mixture:
2.75 g (10 mMole) of bis-1,5-cyclooctadiene nickel
2.65 g (10.1 mMole) of triphenyl phosphane
25.0 g (463 mMole) of butadiene
23.65 g (170 mMole) of N-cyclohexylidene-n-propylamine
8.85 g (101 mMole) of morpholine
86.35 g of toluene.
Reaction temperature: 34° C.
Reaction time: 150 mins.
Conversion of butadiene: 98%
Conversion of N-cyclohexylidene-n-propylamine: 89%
Yield of 1-propylamino-1-(2,5,7-octatrienyl)-cyclohexane, based on the N-cyclohexylidene propylamine: 70%.

EXAMPLE 15

As Example 1, except
Mixture:
8.6 g (9.47 mMole) of bis-1,5-cyclooctadiene nickel
5.0 g (19.08 mMole) of triphenyl phosphane
34.3 g (635 mMole) of butadiene
48.5 g (348.8 mMole) of N-cyclohexylidene-n-propylamine
75.3 g of cyclohexane.
Reaction temperature: 70° C.
Reaction time: 4 h
Conversion of butadiene: 98%
Conversion of cyclohexylidiene propylamine: 92%
Yield of 1-propylidene amino-1-(2,7-octadienyl)-cyclohexane, based on the cyclohexylidene propylamine: 51.8%

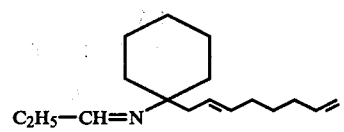

EXAMPLE 16

As Example 1, except
Mixture:
1.0 g (3.64 mMole) of bis-1,5-cyclooctadiene nickel
1.0 g (3.82 mMole) of triphenyl phosphane
14.5 g ( mMole) of butadiene
13.2 g ( mMole) of N-butylidene propylamine
43.35 g of toluene.
Reaction temperature: 40° C.
Reaction time: 20 mins.
Conversion of butadiene: 56%
Conversion of N-butylidene propylamine: 50%
Yield of 9-propylidene amino-9-propyl-1,6-nonadiene, based on the N-butylidene propylamine: 89% 9-propylidene amino-9-propyl-1,6-nonadiene, b.p. 56° C./10$^{-4}$ Torr
IR-spectrum (film): 910, 970 cm$^{-1}$ (HC=CH$_2$); 1640 cm$^{-1}$

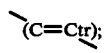

1667 cm$^{-1}$ (>C=N—)
$^1$H-NMR-spectrum (60 MHz) τ [ppm]: 2.5 (m); 4.0 (m); 4.5 (m); 5.0 (m); 6.6 (t); 7.4 (m); 7.85 (m); 8.5 (m); 9.0 (m)
Ratio: 1:1:2:2:1:2:6:6:6

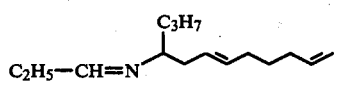

EXAMPLE 17

Catalytic co-oligomerisation of butadiene with acetaldehyde dimethyl hydrazone

As Example 1, except
Mixture:
2.75 g (10 mMole) of Ni(COD)$_2$
2.6 g (9.9 mMole) of triphenyl phosphane
36.55 g (1040 mMole) of butadiene 43.2 g (500 mMole) of acetaldehyde dimethyl hydrazone
0.9 g (10 mMole) of morpholine
83.8 g of toluene.
Reaction temperture: 40° C.
Reaction time: 24 h
Total volume contraction: 10%

After deactivation of the catalyst and distillation, the mixture was examined by gas chromatography.

| Fraction I: 174.1 g (b.p.: up to 30° C./10⁻⁴ Torr) | | |
|---|---|---|
| Acetaldehyde dimethyl hydrazone | 4.5% | 7.8 g |
| Toluene | 48.1% | 83.7 g |
| Vinyl cyclohexene | 3.6% | 6.3 g |
| COD-1,5 | 7.6% | 13.2 g |
| CDT-ttt | 12.2% | 21.3 g |
| CDT-ttc | 1.5% | 2.6 g |
| Σ? (12 peaks) | 22.4% | 39.1 g |
| | 99.9% | 174.0 g |
| Fraction II: 18.5 g (b.p.: up to 65° C./10⁻⁴ Torr) | | |
| CDT-tcc | 21.8% | 4.0 g |
| 2:1-adduct A | 39.3% | 7.3 g |
| 2:1-adduct B | 18.3% | 3.4 g |
| Σ? (23 peaks) | 20.6% | 3.8 g |
| | 100.0% | 18.5 g |
| Fraction III: 4.6 g (b.p.: up to 102° C./10⁻⁴ Torr) | | |
| 2:1-adduct B | 58.3% | 2.7 g |
| Σ? | 41.7% | 1.9 g |
| | 100.0% | 4.6 g |

Residue 16.9 g, without catalyst component 11.5 g
Conversion of butadiene: 100%
Conversion of acetaldehyde dimethyl hydrazone: 82%

Yield of 2:1-adducts A and B: 68.7 mMole = 16.4%, based on the acetaldehyde dimethyl hydrazone reacted.

The 2:1-adduct A was isolated by preparative gas chromatography.
Yield: 89.7%
IR-spectrum (film): 897, 1001, 3080 cm⁻¹ (=CH₂); 967 cm⁻¹

$\diagdown$(C=C$\diagdown$ trans)

UV-spectrum: 229.5 nm (diene absorption)

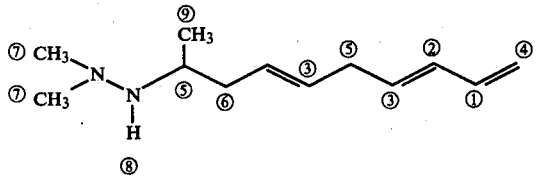

A
¹H-NMR-spectrum (100 MHz):

| Type of proton | Protons calc. | observed | τ [ppm] |
|---|---|---|---|
| ① | } 1.8 | 2 | 3.8 m |
| ② | | | 4.07 m |
| ③ | } 5.5 | 3 | 4.65 m |
| ④ | | 2 | 5.1 m |
| ⑤ | 3.3 | 3 | 7.3 m |
| ⑥ | 1.9 | 2 | 1.9 m |
| ⑦ | 5.6 | 6 | 5.8 s |
| ⑧ | 0.9 | 1 | 8.87 m |

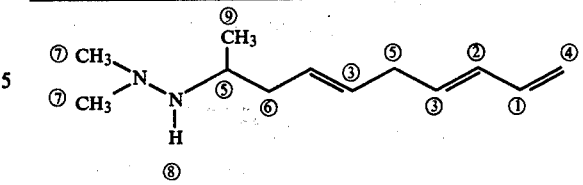

A
¹H-NMR-spectrum (100 MHz):

| Type of proton | Protons calc. | observed | τ [ppm] |
|---|---|---|---|
| ⑨ | 3.0 | 3 | 9.01 d |

C₁₂H₂₂N₂ (194.32)
MS (70 ev): m/e = 194 (M⁺); 87 (M-C₈H₁₁)

The 2:1-adduct B was isolated by preparative gas chromatography.
Purity: 89.6%
IR-spectrum (Film): 994 cm⁻¹ (C=C conj.); 962 cm⁻¹

$\diagdown$(C=C$\diagdown$ trans);

895 (=CH₂)
Raman spectrum: 1636 cm⁻¹ (C=C)
UV-spectrum: 266.6 nm (triene absorption)
¹H-NMR-spectrum (60 MHz):

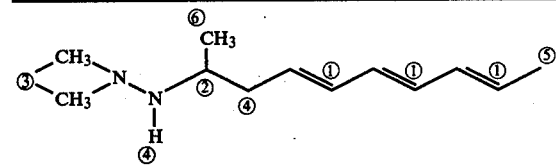

B

| Type of proton | Protons calc. | observed | τ [ppm] |
|---|---|---|---|
| ① | 5.65 | 6 | 4.02 m |
| ② | } 10.03 | 10 | 7.22 t |
| ③ | | | 7.70 s |
| ④ | | | 7.95 m |
| ⑤ | 3.08 | 3 | 8.30 d |
| ⑥ | 3.21 | 3 | 9.04 d |

C₁₂H₂₂N₂ (194.32)
MS (70 eV) m/e = 194 (M⁺); 87 (M—C₈H₁₁)

EXAMPLE 18

Catalytic co-oligomerisation of butadiene with glyoxal-bis-dimethyl hydrazone

As Example 1, except

| Mixture: | 2.75 g | (10 mMole) of Ni(COD)₂ |
|---|---|---|
| | 2.8 g | (10 mMole) of tricyclohexyl phosphane |
| | 37.6 g | (700 mMole) of butadiene |
| | 0.9 g | (10 mMole) of morpholine |
| | | (350 mMole) of |
| | 49.65 g | glyoxyl-bis-dimethyl hydrazone |
| | 175.50 g | |

Reaction temperature: 60° C.
Reaction time: 18 h

Total volume contraction: 3%
Following deactivation of the catalyst and distillation, the mixture was examined by gas chromatography.

Fraction I: 112.1 g (b.p.: up to 37° C./10⁻⁴ Torr)

| | | |
|---|---|---|
| Butadiene | 21.2% | 23.8 g |
| VCH | 0.7% | 0.7 g |
| Toluene | 68.1% | 76.3 g |
| COD-1,5 | 9.0% | 10.1 g |
| Σ? (7 peaks) | 1.0% | 0.1 g |
| | 100.0% | 111.0 g |

Fraction II: 37.2 g (b.p.: 55° C./10⁻⁴ Torr)

| | | |
|---|---|---|
| Toluene | 6.0% | 2.2 g |
| Glyoxal-bis-dimethyl hydrazone | 89.5% | 33.3 g |
| Σ? (8 peaks) | 4.5% | 1.7 g |
| | 100.0% | 37.2 g |

Fraction III: 15.1 g (b.p.: 85° C./10⁻⁴ Torr)

| | | |
|---|---|---|
| Glyoxal-bis-dimethyl hydrazone | 4.2% | 0.6 g |
| 2:1-adduct | 88.7% | 13.4 g |
| Σ? (8 peaks) | 7.1% | 1.1 g |
| | 100.0% | 15.1 g |

Residue: 8.9 g, without catalyst component 3.35 g.
The 2:1-adduct was purified by distillation.
Purity: 96.7% (GCH6).
Conversion of butadiene: 36.71%
Conversion of glyoxal-bis-dimethyl hydrazone: 31.7%
Yield, based on glyoxal-bis-dimethyl hydrazone: 50%
IR-spectrum (film): 1600, 1655 cm⁻¹ (C=C); 965 cm⁻¹

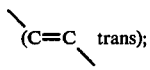

885, 1010, 3085 cm⁻¹ (HC=CH₂); 3180 cm⁻¹ (>NH)
¹H-NMR-spectrum (100 MHz):

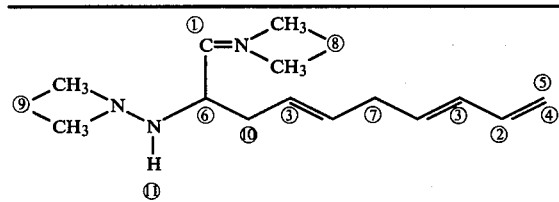

| Type of proton | Protons calc. | observed | τ [ppm] |
|---|---|---|---|
| ① | } 1.7 | 1 | 3.44 m |
| ② | | 1 | 3.68 m |
| ③ | 4.5 | 4 | 4.59 m |
| ④ | } 2.1 | 1 | 5.0 mm |
| ⑤ | | 1 | 5.12 m |
| ⑥ | 1.0 | 1 | 6.30 m |
| ⑦ | } 8.1 | 2 | 7.23 m |
| ⑧ | | 6 | 7.37 s |
| ⑨ | | | 7.69 s |
| ⑩ | } 8.6 | 9 | 7.73 m |
| ⑪ | | | 7.82 m |

C₁₄H₂₆N₄ (250.39)
Calculated C 67.2 H 10.3 N 22.3.
Observed C 67.16 H 10.32 N 22.45.

MS (70 eV): m/e=250 (M⁺); 191 (M—(CH₃)₂N-N); 143 (M—C₈H₁₁)

EXAMPLE 19

20 ml of 5 N-hydrochloric acid are added with stirring to 5.7 g of 9-propylidene amino-9-phenyl-1,6-nonadiene. The homogeneous brown solution is heated for 15 minutes and washed neutral with KHCO₃. The organic phase is extracted with ether. The ether is distilled off and the amine formed is recondensed at 10⁻⁴ Torr.
B.p.: 52° C./10⁻⁴ Torr
Yield: 3.1 g of 9-amino-9-phenyl-1,6-nonadiene

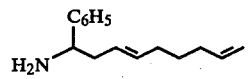

IR-spectrum: 907, 990, 1635 cm⁻¹ (HC=CH₂); 965, 1682 cm⁻¹

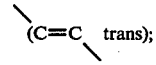

3290, 3370 cm⁻¹ (—NH₂)
¹H-NMR-spectrum (60 MHz) τ [ppm]: 2.8 (m); 4.15 (m); 4.65 (m); 5.1 (m); 6.2 (t); 7.85 (m); 8.5 (m); 9.1 (m)
Ratio: 5:1:2:2:1:6:2:2

EXAMPLE 20

As Example 1, except
Mixture:
3.05 g (11.1 mMole) of bis-1,5-cyclooctadiene nickel
2.9 g (11.1 mMole) of triphenyl phosphane
41.6 g (770 mMole) of butadiene
53.6 g (362.2 mMole) of benzaldehyde dimethyl hydrazone
81.6 g of toluene.
Reaction temperature: 40° C.
Reaction time: 24 h
Conversion of butadiene: 98%
Conversion of benzaldehyde dimethyl hydrazone: 89%
Yield of phenyl-2,7-octadienyl ketone dimethyl hydrazone, based on the benzaldehyde dimethyl hydrazone reacted: 65%
IR-spectrum: 915 cm⁻¹ (HC=CH₂); 1565 cm⁻¹ (N=C); 965 cm⁻¹

¹H-NMR-spectrum (60 MHz) τ [ppm]: 2.5 (m); 3.0 (m); 4.0 (m); 4.7 (m); 5.1 (m); 7.2 (s); 8.0 (m); 8.4 (m)
Ratio: 2:3:1:2:2:6:2:6

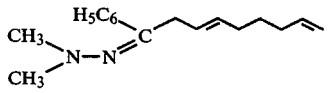

EXAMPLE 21

As Example 1, except

Mixture:
- 2.45 g (8.3 mMole) of bis-1,5 cyclooctadiene nickel
- 2.35 g (9.0 mMole) of triphenyl phosphane
- 43.5 g (805 mMole) of butadiene
- 36.8 g (249 mMole) of N-benzylidene-n-propylamine
- 0.75 g (19.7 mMole) of lithium aluminium hydride
- 69.8 g of toluene.

Reaction temperature: 40° C.
Reaction time: 110 mins.
Conversion of butadiene: 34%
Conversion of N-benzylidene-n-propylamine: 40%
Yield of 9-propylamino-9-phenyl-2,6-nonadiene, based on the N-benzylidene-n-propylamine reacted: 20%

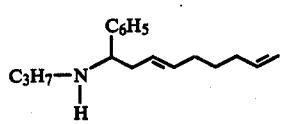

What is claimed is:

1. A process which comprises condensing a 1,3-diene of the formula

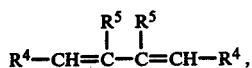

wherein $R^4$ and $R^5$, independently of one another, represent hydrogen or an alkyl group having 1 to 4 carbon atoms with a Schiff base of the formula

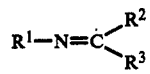

wherein each of $R^1$, $R^2$ and $R^3$ represents hydrogen, alkyl having 1 to 12 carbon atoms, cycloalkyl having 5 to 7 ring members, aralkyl in which the aryl portion is carbocyclic and has up to 10 ring members and the alkyl portion has up to 7 carbon atoms; or dimethylamino or dimethylamino substituted by alkyl ethers having up to 12 carbon atoms, alkyl esters having up to 12 carbon atoms or C=N double bonds, in the presence of a nickel (O)—containing catalyst, and optionally in the presence of a conventional electron donor and a conventional weakly H-acid compound, said weakly H-acid compound being a primary or secondary amine, a cycloalkyl amine having 4 to 8 ring members, a carbocyclic arylamine having up to 10 ring members, a mono- or di-azacyclic carbocyclic amine having 5 to 7 ring members, and unsaturated carbocyclic cycloalphatic amine having up to 3 double bonds and optionally N-alkylated wherein the N-alkyl portion has up to 7 carbon atoms, an alkyl- or aryl-phosphor hydrogen compound, an alcohol, an organic acid or water, with a molar ratio of Ni: weakly H-acid compound of from 1:0 to 1:10.

2. A process as claimed in claim 1 wherein the weakly H-acid compound is a primary or secondary amine, a phosphane, an alcohol, an organic acid or water.

3. A process as claimed in claim 1, wherein the H-acid compound is morpholine, N-methyl aniline, piperidine, piperazine, pyrrolidine, diethylamine, cyclohexylamine, propylamine, aniline, 9-propylamino-1,3,6-octatriene, methanol, ethanol, t-butanol, cyclohexanol, phenol, isopropyl phenyl phosphane, diphenyl phosphane, phenyl phosphane, diisopropyl phosphane, cyclohexyl phosphane, acetic acid, propionic acid or adipic acid.

4. A process as claimed in claim 1 wherein said weakly H-acid compound is present in a molar ratio of Ni: weakly H-acid compound of from $1:10^{-3}$ to $1:10^2$.

* * * * *